United States Patent [19]

Cohen et al.

[11] Patent Number: 4,795,642
[45] Date of Patent: Jan. 3, 1989

[54] GELATIN-ENCAPSULATED CONTROLLED-RELEASE COMPOSITION

[75] Inventors: Jonathan M. Cohen, Matawan; Ira R. Berry, Westfield; Lionel Borkan, New Vernon, all of N.J.

[73] Assignee: Pharmacaps, Inc., Elizabeth, N.J.

[21] Appl. No.: 85,795

[22] Filed: Aug. 17, 1987

Related U.S. Application Data

[62] Division of Ser. No. 858,969, May 1, 1986, Pat. No. 4,708,834.

[51] Int. Cl.$^4$ .......................... A61K 9/52; A61K 9/66; B01J 13/02
[52] U.S. Cl. ..................... 424/455; 264/4.3; 424/456; 424/460; 424/461; 424/DIG. 15; 428/402.2; 428/402.24; 514/944; 514/963; 514/965
[58] Field of Search ....................... 264/4.3; 428/402.2; 424/456, 460, 461, 455; 514/944

[56] References Cited

U.S. PATENT DOCUMENTS

| | | | |
|---|---|---|---|
| 2,963,402 | 12/1960 | Nalin et al. | 424/494 |
| 3,136,695 | 6/1964 | Tansey | 424/443 |
| 3,228,789 | 1/1966 | Glassman | 427/3 |
| 3,325,472 | 6/1967 | Sackler et al. | 536/114 |
| 3,361,632 | 1/1968 | Ross et al. | 424/457 |
| 3,400,197 | 9/1968 | Lippmann | 424/469 |
| 3,492,397 | 1/1970 | Peters et al. | 424/495 |
| 3,493,652 | 2/1970 | Hartman | 424/94 |
| 3,558,768 | 1/1971 | Klippel | 424/494 |
| 3,574,020 | 4/1971 | Johnson et al. | 424/423 |
| 3,851,051 | 11/1974 | Miskel et al. | 424/455 |
| 3,909,444 | 9/1975 | Anderson et al. | 428/402.24 |
| 4,153,677 | 5/1979 | John | 424/495 |
| 4,173,626 | 11/1979 | Dempski et al. | 424/462 |
| 4,199,560 | 5/1980 | Gyarmati et al. | 424/459 |
| 4,259,315 | 3/1981 | Lippmann et al. | 424/459 |
| 4,344,968 | 8/1982 | Aoda et al. | 424/81 |
| 4,391,909 | 7/1983 | Lim | 435/178 |
| 4,421,736 | 12/1983 | Walters | 424/459 |
| 4,474,752 | 10/1984 | Haslam et al. | 424/78 |
| 4,486,412 | 12/1984 | Shah et al. | 424/156 |
| 4,690,816 | 9/1987 | Hata et al. | 424/456 |
| 4,708,834 | 11/1987 | Cohen et al. | 264/4.3 |

FOREIGN PATENT DOCUMENTS

| | | | |
|---|---|---|---|
| 1467864 | 1/1969 | Fed. Rep. of Germany | 424/492 |
| 0206515 | 12/1983 | Japan . | |
| 1008044 | 10/1965 | United Kingdom | 264/4.3 |

*Primary Examiner*—Richard D. Lovering
*Attorney, Agent, or Firm*—Merchant, Gould, Smith, Edell, Welter & Schmidt

[57] ABSTRACT

A controlled-release pharmaceutical unit dosage form is provided comprising a gelatin capsule enclosing a solid matrix formed by the cation-assisted gellation of a liquid fill incorporating vegatable gum and a pharmaceutically-active compound, as well as methods for the preparation thereof.

19 Claims, 2 Drawing Sheets

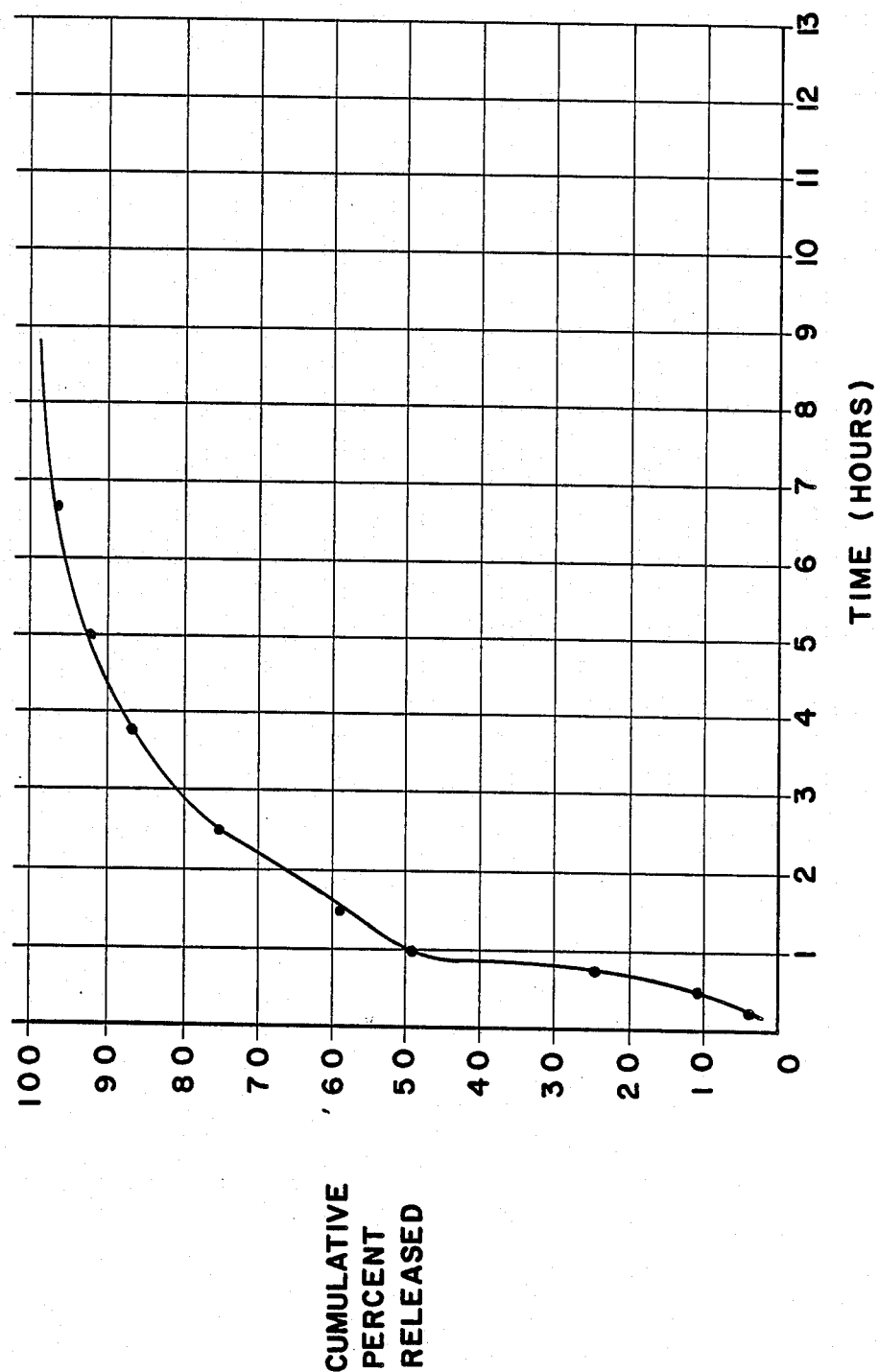

GELATIN-ENCAPSULATED CONTROLLED-RELEASE COMPOSITION

This is a division of application Ser. No. 858,969, filed May 1, 1986, and now U.S. Pat. No. 4,708,834.

BACKGROUND OF THE INVENTION

Soft gelatin encapsulation of a solution or dispersion of a pharmaceutical agent in a liquid carrier or a water-soluble gel offers many advantages over other dosage forms such as coated or uncoated compressed solid tablets or bulk liquid preparations. Gelatin encapsulation of a solution or dispersion permits the accurate delivery of a unit dose, an advantage which becomes especially important when relatively small amounts of the active ingredient must be delivered, as in the case of certain hormones. Such accuracy is more difficult to achieve via a tabletting process wherein solids must be uniformly mixed and compressed, or by incorporation of the total dose of the active ingredient into a bulk liquid carrier which must be measured out prior to each oral administration.

Soft gelatin encapsulation provides a dosage form which is more readily accepted by patients, since the capsules are easy to swallow and need not be flavored in order to mask the unpleasant taste of the active principle. Soft gelatin capsules are also more easily transported by patients than bulk liquids since only the required number of doses need be removed from the package.

Soft gelatin encapsulation further provides the potential to improve the bioavailability of pharmaceutical agents in the gastrointestinal tract. In the case of an oral liquid preparation, a significant amount of the active ingredient may be lost in the mouth or esophageal lining, prior to absorption into the blood. In contrast, with soft gelatin capsules, the active ingredients are rapidly released as soon as the gelatin shell ruptures. Complete disintegration and dissolution of the capsule are not necessary for the active ingredients to become available for absorption as in the case of tabletted compositions. Also, relatively insoluble active ingredients can be dispersed in a liquid or gelled carrier to provide faster absorption. For example, Miskel et al. (U.S. Pat. No. 3,851,051) discloses soft gelatin capsules which contain aqueous solutions or suspensions of active ingredients in a water-soluble gel lattice matrix which is formulated to rapidly disperse upon rupture of the capsule shell. The rapid action of the active ingredient is ascribed to the high water content of the simple gel (5-20%) and the absence of an oil vehicle. The encapsulation of solutions or dispersions of biologically-active compounds in soft gelatin capsules is disclosed in U.S. Pat. Nos. 4,486,412 and 3,784,684.

Formulations intended for the controlled release of pharmaceutically-active compounds in vivo include solid particles of the active ingredient which are coated or tabletted with film-forming polymers, waxes, fats, silica, and the like. These substances are intended to inhibit the dissolution, dispersion or absorption of the active ingredient in vivo. Although these compositions might be encapsulated in soft gelatin with equipment modifications, the use of such controlled release medicaments can negate many of the advantages associated with the use of liquid filling compositions, such as the ability to uniformly deliver an accurate dose of the active ingredient.

Therefore, a need exists for controlled-release compositions which are suitable for, and compatible with, soft gelatin encapsulation.

A further need exists for gelatin-encapsulated compositions which can release an accurate dose of a medicament therefrom at a controlled rate following rupture of the capsule shell. A need also exists for methods for the preparation of gelatin-encapsulated, controlled-release compositions which can uniformly deliver a unit dose of one or more pharmaceutically active compounds in vitro or in vivo.

BRIEF DESCRIPTION OF THE INVENTION

The present invention provides a pharmaceutical unit dosage form comprising a gelatin capsule enclosing a water-soluble or dispersible gelled polymeric matrix. The matrix is capable of the controlled release of a pharmaceutically-active compound therefrom at a substantially constant rate when the capsule is ruptured in an aqueous medium. The polymeric matrix is not formed by simple coacervation as are the quick-release gels disclosed in the Miskel et al. patent, but rather, is formed by the metal or ammonium cation-promoted gellation of a liquid fill, following its encapsulation in the gelatin capsule. The fill comprises an aqueous solution or dispersion of a polysaccharide gum, such as a colloidal dispersion of a vegetable gum. The gellable fill also includes the active compound and optional amounts of co-solvents, buffers, surfactants, thickeners and the like.

Thus, the present invention is directed to a pharmaceutical unit dosage form prepared by a process comprising:

(a) forming a liquid fill comprising an aqueous solution or dispersion of a polysaccharide gum and a pharmaceutically-active compound wherein the solution or dispersion optionally includes an alcohol;

(b) encapsulating said liquid fill in a gelatin capsule; and (c) gelling said liquid fill with an effective amount of a cationic gelling agent.

In a preferred embodiment of the present invention, the cationic gelling agent is incorporated entirely in the gelatin shell, and acts to gel the liquid fill after the fill has been enclosed in the shell. This novel formulation method obviates the problems associated with handling fills in which the gelling process is initiated prior to the encapsulation step. The present invention is also directed to the method of forming the controlled-release pharmaceutical unit dosage form.

Therefore, the present dosage form can be used as an ingestible capsule or as a suppository, to accomplish the controlled release of therapeutic agents into physiological media such as gastric fluid, mucus, saliva, vaginal fluid, rectal secretions and the like. The gelled matrix can stabilize the active ingredient and releases the active ingredient at a controlled rate which maintains a uniform level of effective concentrations of the active ingredient. This controlled release can reduce the side effects due to initial overdosage, prevent wastage of the active ingredient and provide better patient compliance.

As employed herein with respect to the active ingredient, the term "controlled release" or "prolonged release" is intended to mean that the present capsules require at least an hour to release a major portion of the active ingredient into the surrounding medium, e.g., about 1-3 hours.

In the following description of the invention, all percentages and parts are by weight unless otherwise noted.

BRIEF DESCRIPTION OF THE DRAWINGS

FIG. 2 is a graphical representation of the rate of release of niacin from a unit dosage form of the invention.

DETAILED DESCRIPTION OF THE INVENTION

Figure 1:
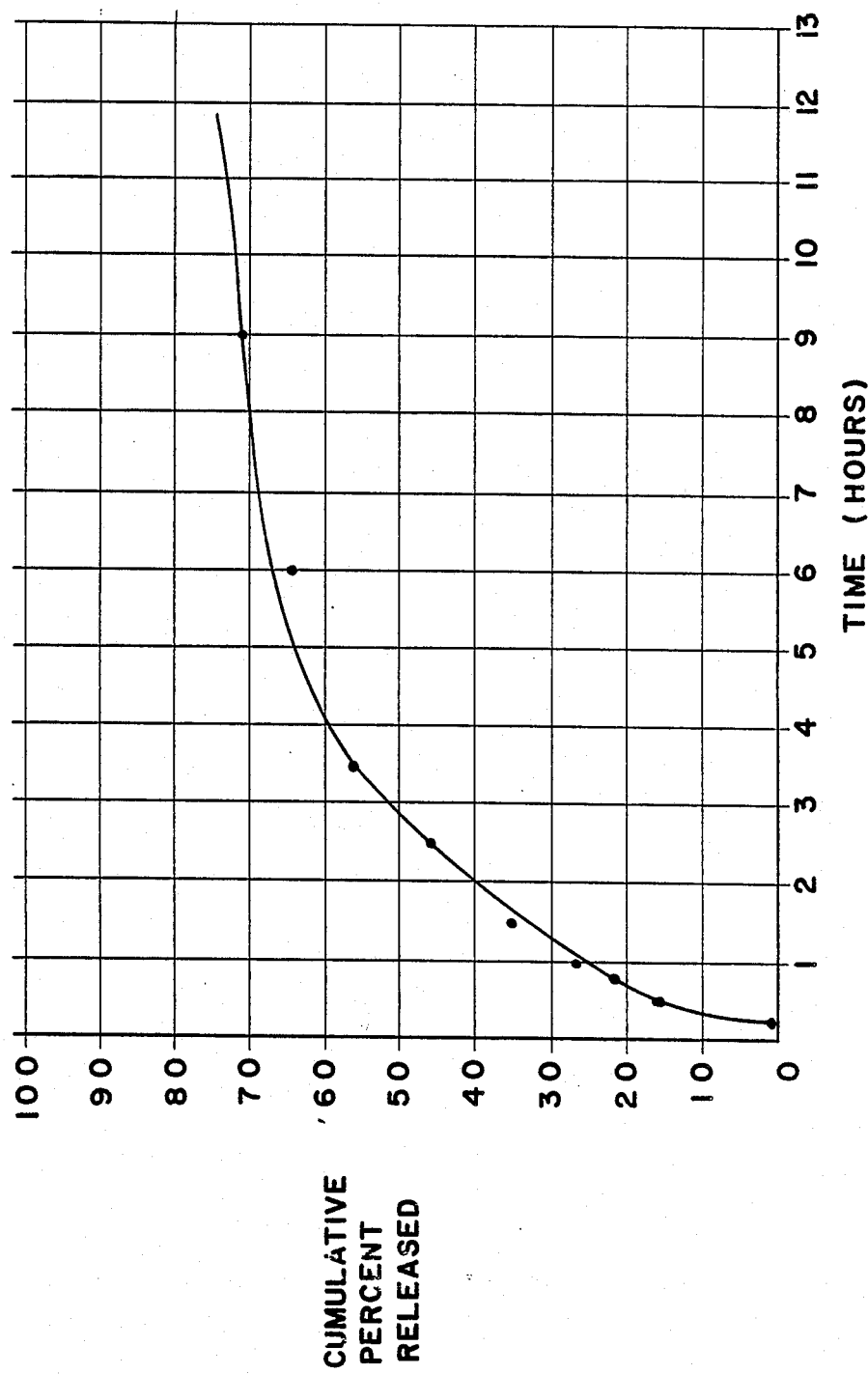
FIG. 1 is a graphical representation of the rate of release of acetaminophen from a unit dosage form of the invention.

In accord with the present invention, a liquid fill composition is prepared by forming an aqueous solution or dispersion of a gellable polysaccharide gum and a pharmaceutically-active compound.

Polysaccharide Gum

The polysaccharide gums which are useful to form the polymeric matrices of the invention are selected from those organic gums which gel or coagulate when solutions or dispersions thereof are contacted with metal or ammonium cations. Preferred gums for use in the present invention include vegetable gums, such as the alkali metal salts of alginic acid ("alginates"), carrageenan (preferably kappacarrageenan), pectin, and mixtures thereof. These "strong gums" re-gel from solution or dispersion to yield a continuous gel structure which is suitable as the polymeric matrix of the invention.

Gelling Agent

The present gum-containing liquid fills are gelled following their encapsulation by means of an effective amount of one or more cationic gelling agents. These agents comprise alkali metal, alkaline earth metal or ammonium cations. Useful divalent cationic gelling agents also include copper (II), cadmium (II), barium (II), strontium (II), cobalt (II), nickel (II), zinc (II), manganese (II) and iron (II) cations. Useful trivalent cations include aluminum (III), chromium (III) and iron (III). Also useful are heavy metal compounds which yield mobile ions in solution. Preferred water-soluble ionic compounds are selected from pharmaceutically-acceptable fluorides, citrates, phosphates, tartrates, sulfates, acetates, borates, chlorides and the like, of cations such as sodium, lithium, potassium, magnesium, calcium and ammonium. Especially preferred gelling agents include inorganic salts, i.e., chloride salts such as potassium chloride (KCl), calcium chloride (CaCl$_2$) and mixtures thereof.

Solvent

The present hydrophillic liquid fills are prepared by dispersing or dissolving the gellable gum in an aqueous solvent system which may also include one or more alcoholic co-solvents such as alkanols or glycols.

Therefore, the present solvent systems will contain amounts of water which can act to hydrate the vegetable gum or gums which are employed. For a given liquid fill, the amount of water is adjusted so that it does not deleterously effect the stability of the gelatin capsule wall of the finished product.

Alcohols which can be employed in the present invention include liquid polyethylene glycols, i.e., polyethylene glycol-200, 300, 400 or 600, wherein the suffixed numbers indicate the approximate molecular weight of the glycol. Although a polyethylene glycol can be employed as the sole alcoholic solvent for the fill components, it is often desirable to adjust the viscosity and solubilization power of the primary solvent by the use of co-solvents. Useful co-solvents include other alcohols, for example:

(a) lower (alkanols), such as ethanol and isopropanol;

(b) $C_2$–$C_4$ polyols, such as a diol or triol, e.g., propylene glycol, glycerol or mixtures thereof, or (c) derivatives thereof, e.g., propylene carbonate, lower(alkyl) glycol ethers and the like. In some cases, mixtures of alkanols, polyols or their derivatives [classes (a)–(c)] can replace the liquid polyethylene glycol component.

Pharmaceutically-Active Ingredient

The liquid fill can incorporate one or more pharmaceutically-active compounds which will be dispersed or dissolved in the solvent base of the fill in amounts which can vary widely depending upon the biological activity, the solubility of the active component and the desired rate of release of the active component from the gelled matrix. Useful classes of pharmaceutically-active compounds which can be delivered by the present dosage forms include analgesics, calcium channel blockers, beta-blockers, antibacterials, antidepressants, antidiabetics, anti-inflammatory agents, cerebral stimulants, sedatives, anti-parasitics, decongestants, muscle relaxants, anti-Parkinsonism agents, bronchodilators, vitamins and dietary supplements such as minerals, fatty acids and the like.

Bulking Agents

Bulking agents are optionally included in the fill to adjust the release rate of the pharmaceutical compound from the final gelled polymeric matrix. Bulking agents include, but are not limited to, starches, natural and synthetic cellulosic derivatives such as methyl, ethyl, propyl, hydroxymethyl, hydroxyethyl, hydroxypropyl or hydroxypropylmethylcelluloses, silica and other natural and synthetic silicic acid analogues, other vegetable gums such as iota-carrageenan, lambda-carrageenan, tragacanth, karaya, ghatti, guar, tamarind, psyllium, quince, larch, and the like. Although some of these gums can gel to some extent by coacervation, they do not cation-gel to the degree required to yield a solid matrix which is effective for the controlled release of the active ingredient in vivo.

Dispersing Agents

The fill component of the present invention may optionally comprise minor but effective amounts of one or more dispersing agents. The release rate of active ingredients which are insoluble or exhibit low solubility in the aqueous solvent system can be enhanced by the use of these dispersants.

Useful dispersants include nonionic surfactants such as the $C_{12}$–$C_{20}$ fatty acid esters of sorbitol and its anhydrides ("Spans") optionally co-polymerized with about 15–90 moles of ethylene oxide ("Tweens"). Typical polysorbates which aid in the formation of the present dispersions and can help to stabilize the gelatin capsule include polysorbate 20 (a laurate ester); polysorbate 40 (a palmitate ester); polysorbate 60 (a mixture of stearate and palmitate esters); and polysorbate 80 (an oleate ester) wherein the suffixed numbers indicate the approximate mole ratio of ethylene oxide to sorbitol. For a general discussion of the properties and composition of the polyethylene glycols and the polysorbates, see Remington's Pharmaceutical Sciences, A. Osol, ed., Mack Pub. Co. (16th ed. 1980) at pages 1252-1253, the disclosure of which is incorporated by reference herein. Other useful dispersing agents include triglycerides of long or medium chain length such as lecithin and vegetable oils such as palm oil, coconut oil, corn oil, soybean oil and the like. Waxes such as high molecular weight polyethylene glycols (m.w. 1000-8000), beeswax, spermaceti, lanolin, ouricuri and the like can also function as dispersing agents within the context of the present invention. The dispersing agents may be present in an amount from about 1-20% by weight of the capsule contents.

Therefore, preferred liquid fill compositions for use as the gel-matrix precursors will comprise about 0.1-20%, preferably about 2-10.0% of the cation-gellable polysaccharide gum; about 0.05-5%, preferably about 0.1-2.5% of a cationic gelling agent comprising a metal cation or ammonium ion; and about 0.0001-90%, preferably about 0.1-75% of a pharmaceutically-active compound. These components are dispersed or dissolved in an aqueous solvent system. Thus, the liquid fill will comprise about 5-75%, preferably about 20-50% water and optionally, about 5-60%, preferably about 7.5-40% of propylene carbonate or a liquid polyethylene glycol, and about 1-15% of a $C_2$-$C_4$-polyol, a lower(alkanol) or mixtures thereof. The present liquid fills also can include about 0.1-90%, preferably about 0.3-25%, of a bulking agent such as methyl or ethyl cellulose, a "weak" vegetable gum, or mixtures thereof, as well as minor but effective amounts of buffers such as citrates, fumarates, adipates and the like.

Encapsulation

The liquid fill can be prepared by adding the gellable gum along with the bulking agent and buffers, if any, to the pre-formed solvent system, with agitation as necessary, followed by addition of one or more active ingredients. Although the gelling agent can be incorporated into the liquid fill at this point, it is preferable to incorporate a part or, most preferably, all of the gelling agent into the plasticized gelatin which is employed to encapsulate the fill. Following encapsulation of a suitable amount of the homogeneous liquid fill, the gelling agent is brought into contact with the dispersed or dissolved gum and acts to resolidify it to yield a coherent gelled matrix. The matrix incorporates the active compound uniformly dispersed throughout.

The capsules are dried to the extent that the residual water in the gelled fill does not deleteriously affect the capsule wall, e.g., until about 0.5-12%, preferably about 2.5-7.5% by weight of water is present in the fill.

Although encapsulation of the present fill materials in soft gelatin capsules is preferred, the present method can also be employed to gel fill materials which have been encapsulated in two-piece hard gelatin capsules or in soft gelatin suppositories, e.g., for the vaginal, rectal, sublingual or buccal administration of the present pharmaceutical dosage forms. In addition to gelatin, the capsule wall can include water and an effective amount of plasticizer such as glycerin, sorbitol or mixtures thereof. The shell of the present capsules can also include minor but effective amounts of opacifiers, coloring agents, preservatives and the like.

The invention will be further described by reference to the following detailed examples.

EXAMPLE I—ACETAMINOPHEN DOSAGE FORM

A. Fill Composition

Acetaminophen: 500 parts
Sodium Alginate: 15 parts
Kappa-Carrageenan: 41 parts
Iota-Carrageenan: 5 parts
Water: 468 parts
Polyethylene Glycol 400: 468 parts

B. Soft Gelatin Shell

Gelatin: 199 parts
Glycerin: 72 parts
Water: 146 parts
$CaCl_2$: 3 parts
KCl: 5 parts

C. Fill Preparation

The gums, water and polyethylene glycol are combined in a suitable vessel and agitated until a uniform mixture results. The acetaminophen is added, and agitation is continued for about 45 min. The liquid blend is then milled.

D. Shell Preparation

Gelatin, glycerin and water are added to a suitable vessel and agitated with heat until a uniform melt results. The $CaCl_2$ and the KCl are then added to the molten gelatin.

E. Encapsulation

The shell preparation was employed to encapsulate 1200 mg portions of the liquid fill blend employing rotary die encapsulation (#20 oval die) to yield one-piece hermetically-sealed, soft gelatin capsules. Following encapsulation, the liquid fill gelled to a solid mass which completely filled the interior of the capsule. The gelled polymeric matrix contained 4.3% water.

F. Release Profile Study

A USP paddle-type dissolution apparatus was filed with 900 ml of 0.1N HCl and four of the acetaminophen capsules were placed in each of the six chambers of the apparatus. The 0.1N HCl was stirred at 100 rpm and samples of the test fluid were withdrawn periodically and analyzed spectrophotometrically ($\lambda$ max=244 nm), employing reference standards to yield the curve depicted in FIG. 1. The data summarized in FIG. 1 establish that the gelled matrix of the capsule of Example I is effective for the controlled release of acetaminophen, releasing 50% of the total drug in about 3.0 hrs and 70% after about 7.5 hours.

It is also expected that the dosage form of Example I will be particularly effective for the controlled release of other active ingredients such as ibuprofen, acetohexamide, tolbutamide, diflunisal, carisoprodol, theophylline, dyphylline, difedipine and digoxin.

EXAMPLE II—NIACIN DOSAGE FORM

A. Fill Composition

Niacin: 1200 parts
Sodium Alginate: 120 parts
Propylene Glycol: 200 parts
Polyethylene Glycol 400: 450 parts
Glycerin: 125 parts
Ethyl Cellulose: 500 parts Methyl Cellulose: 25 parts
Ethanol: 155 parts
Water: 1,630 parts

B. Soft Gelatin Shell

Gelatin: 768 parts
Glycerin: 385 parts
Water 477 parts

C. Salt Solution

KCl: 9 parts
CaCl$_2$: 16 parts
Water: 85 parts

D. Encapsulation

The fill and shell formulations are prepared as described for Example I, above, with the exception that the salts were added to the molten gelatin as the solution of part (C). The shell formulation was employed to encapsulate 500 mg portions of the milled and deaerated liquid fill via rotary die encapsulation (#9, round die) to yield one-piece hermetically-sealed, soft gelatin capsules. Following encapsulation, the liquid fill gelled to a solid mass. The gelled matrix contained 5.7% water.

E. Release Profile Study

The rate of release of niacin from the capsules was determined via the procedures of Example I(F), above, analyzing at a λmax of 263 nm, to yield to curve depicted in FIG. 2. The data summarized in FIG. 2 establish that the gelled matrix of the capsule of Example II is effective for the controlled release of niacin, releasing 60% of the vitamin in about 1.75 hrs and 90% of the vitamin after about 4.5 hours.

It is also expected that the dosage form of Example I will be effective for the controlled release of active ingredients such as codeine, diltiazem, amytriptyline, meclofenemate, ephedrine and phenylpropanolamine.

Although the present invention has been described primarily in terms of the encapsulation of active ingredients which are intended for administration in humans, the use of the present dosage forms for veterinary, biological or industrial applications is also within the scope of the invention.

While certain representative embodiments of the invention have been described herein for purposes of illustration, it will be apparent to those skilled in the art that modifications therein may be made without departing from the spirit and scope of the invention.

What is claimed is:

1. A pharmaceutical unit dosage form comprising a gelatin shell enclosing a gelled polymeric matrix, characterized by having been prepared by the process consisting essentially of:
   (a) forming a liquid fill comprising an aqueous solution or dispersion of a polysaccharide gum and pharmaceutically-active compound;
   (b) encapsulating said liquid fill in a gelatin shell wherein the gelatin shell comprises gelatin, an effective amount of a plasticizer, water and an amount of cationic gelling agent effective to gel said liquid fill; and
   (c) gelling said liquid fill with the cationic gelling agent.

2. The pharmaceutical unit dosage form of claim 1 wherein the polysaccharide gum is selected from the group consisting of alginate, kappa-carrageenan and pectin.

3. The pharmaceutical unit dosage form of claim 1 wherein the gelling agent comprises a metal cation or an ammonium ion.

4. The pharmaceutical unit dosage form of claim 3 wherein the gelling agent comprises a chloride salt.

5. The pharmaceutical unit dosage form of claim 1 wherein the aqueous solution or dispersion further comprises propylene carbonate or a liquid polyethylene glycol.

6. A pharmaceutical unit dosage form comprising a gelatin shell including an effective amount of a gelling agent comprising metal cations or ammonium ions, wherein said shell encloses a water-soluble or water-dispersable gelled polymeric matrix and a pharmaceutically-active compound dispersed throughout said matrix, wherein said matrix is formed in situ by the gellation of a liquid fill comprising an aqueous solution or dispersion of the pharmaceutically-active compound and a polysaccharide gum, by means of said gelling agent, following the encapsulation of the liquid fill, so that the phramaceutically-active compound is released from said gelled polymeric matrix over a prolonged period when said capsule is ruptured in an aqueous medium.

7. The pharmaceutical unit dosage form of claim 6 wherein said gelatin capsule comprises gelatin, an effective amount of a plasticizer, and water.

8. The pharmaceutical unit dosage form of claim 6 wherein said gelatin capsule is a two-piece, hard gelatin capsule.

9. The pharmaceutical unit dosage form of claim 6 wherein said polysaccharide gum comprises a vegetable gum.

10. The pharmaceutical unit dosage form of claim 9 wherein the vegetable gum is selected from the group consisting of alginate, kappa-carrageenan, pectin and mixtures thereof.

11. The pharmaceutical unit dosage form of claim 9 wherein the cationic gelling agent comprises alkali metal cations or alkaline earth metal cations.

12. The pharmaceutical unit dosage form of claim 6 wherein the aqueous solution or dispersion comprises a liquid polyethylene glycol.

13. The pharmaceutical unit dosage form of claim 12 wherein the aqueous solution or dispersion comprises glycerin, propylene glycol or mixtures thereof.

14. The pharmaceutical unit dosage form of claim 12 wherein the aqueous solution comprises a polysorbate or a triglyceride dispersing agent.

15. The pharmaceutical unit dosage form of claim 12 wherein the aqueous solution or dispersion comprises a cellulosic bulking agent.

16. A pharmaceutical unit dosage form comprising a soft gelatin shell including an effective amount of a cationic gelling agent comprising metal cations or ammonium ions, wherein said shell encloses a water-soluble or water-dispersable gelled polymeric matrix and an effective amount of a pharmaceutically-active compound dispersed throughout said matrix, wherein said matrix is formed in situ by the gellation of a liquid fill composition comprising about 0.1-20% of a vegetable gum selected from the group consisting of alginate, kappa-carrageenan, pectin and mixtures thereof; the pharmaceutically-active compound, about 5-60% of a liquid polyethylene glycol, and about 5-75% water; wherein said gellation is accomplished with the cationic gelling agent, following the encapsulation of the liquid fill, so that the pharmaceutically-active compound is released from said gelled polymeric matrix over a prolonged period when said capsule is ruptured in a physiological medium.

17. The pharmaceutical unit dosage form of claim 16 wherein the cationic gelling agent comprises potassium chloride, calcium chloride or mixtures thereof.

18. The pharmaceutical unit dosage form of claim 16 wherein the liquid fill composition further comprises about 1-15% of a $C_2-C_4$ polyol, a lower (alkanol) or mixtures thereof.

19. The pharmaceutical unit dosage form of claim 16 wherein the liquid fill further comprises about 0.1-90% of a bulking agent.

* * * * *